United States Patent [19]

Forte

[11] Patent Number: 5,073,669

[45] Date of Patent: Dec. 17, 1991

[54] METHOD FOR AROMATIC HYDROCARBON RECOVERY

[75] Inventor: Paulino Forte, Yonkers, N.Y.

[73] Assignee: UOP, Des Plaines, Ill.

[21] Appl. No.: 321,033

[22] Filed: Mar. 9, 1989

[51] Int. Cl.$^5$ .......................... C07C 7/00; C10G 17/04
[52] U.S. Cl. .................... 585/808; 585/807; 585/835; 585/857; 585/866; 208/311; 208/321; 208/325; 208/334
[58] Field of Search ............... 585/804, 807, 808, 857, 585/866, 835, 864; 208/321, 311, 334, 325

[56] References Cited

U.S. PATENT DOCUMENTS 3,590,092 6/1971 Uitti et al. ........................ 585/857
3,702,295 11/1972 Thompson ........................ 208/321

*Primary Examiner*—Curtis R. Davis
*Assistant Examiner*—Nhat Phan
*Attorney, Agent, or Firm*—Thomas K. McBride; John G. Tolomei

[57] ABSTRACT

Methods are provided for the recovery of aromatic hydrocarbons from the extract phase of aromatic-selective solvent extraction processes which involve withdrawing a vapor side-cut fraction containing aromatic hydrocarbons and solvents from a stripping zone and passing the side-cut fraction to a rectification zone which can be refluxed with aromatic hydrocarbons or aqueous condensate.

7 Claims, 2 Drawing Sheets

METHOD FOR AROMATIC HYDROCARBON RECOVERY

FIELD OF THE INVENTION

The present invention relates to processes for the recovery of aromatic hydrocarbons from feedstocks utilizing solvent extraction. In particular, the present invention provides improved methods for the recovery of aromatic hydrocarbons from the extract phase from solvent extraction processes.

BACKGROUND OF THE INVENTION

Conventional processes for the recovery of high purity aromatic hydrocarbons such as benzene, toulene and xylenes (BTX) from various hydrocarbon feedstocks including catalytic reformate, hydrogenated pyrolysis gasoline, etc., utilize an aromatic selective solvent. Typically, in the practice of such processes, a hydrocarbon feed mixture is contacted in an extraction zone with an aqueous solvent composition which selectively dissolves the aromatic components from the hydrocarbon feedstock, thereby forming a raffinate phase comprising one or more non-aromatic hydrocarbons, and an extract phase comprising solvent having aromatic components dissolved therein.

A common problem in many aromatics extraction processes is that the extract phase contains, in addition to aromatic hydrocarbons, solvent and contaminating amounts of non-aromatic hydrocarbons from which the aromatics must be recovered. Accordingly, a variety of methods have been proposed to recover the extracted aromatic hydrocarbons while avoiding solvent losses in the aromatic extract product. These methods typically utilize extractive distillation with steam stripping in order to remove the contaminating non-aromatic hydrocarbons from the extract phase followed by another step, e.g., distillation, rectification, washing, in order to remove the solvent from the aromatic hydrocarbons. Several types of recovery methods are hereinafter described.

U.S. Pat. No. 3,590,092 discloses a method for aromatic hydrocarbon recovery that utilizes a single column wherein a side-cut vapor fraction comprising aromatic hydrocarbons and a minor quantity of solvent is withdrawn and introduced into a separate rectifying zone maintained under rectifying conditions, to provide a relatively solvent free aromatic extract product. The side-cut aspect of the method is set forth at col. 6, lines 10 to 43, wherein it is stated that:

"A side-cut vapor fraction is withdrawn via line 25 and passed into rectifying column 32 which is maintained under rectification conditions. Typically, the conditions maintained in rectifying column 32 include a temperature from 200° F. to 250° F. and a pressure from 1 to 10 psig. An overhead stream comprising the desired aromatic hydrocarbons, benzene and toluene, is withdrawn via line 26, condensed in condensor-separator 30, and passed out of the system via line 28. Any water condensed and removed in separator 30 is also removed from the system via line 27. A bottoms fraction comprising primarily sulfolane solvent and heavy aromatic hydrocarbons of the $C_{10}$, $C_{11}$ and $C_{12}$ type (if any) is withdrawn via line 33 and in a preferred embodiment of this invention passed into the lower portion of stripper column 17. Alternatively, a portion of the material in line 33 or all of the material in line 33, if desired, may be passed via line 34 into line 12 as lean solvent suitable for reuse in the extraction zone. Therefore, it can be seen that the lean solvent which in the preferred embodiment of this invention is returned to extractor column 11 via line 12 comprises solvent obtained from the bottom of stripper column 17 and from the bottom of rectifying column 32. A portion of the high purity aromatic hydrocarbon stream in line 28 is diverted via line 31 and passed into the upper section of rectifying column 32 as reflux thereon.

Returning now to stripper column 17, a bottoms fraction comprising lean sulfolane solvent suitable for reuse in the extraction zone is withdrawn via line 12 and in a preferred embodiment of this invention is returned to the upper section of extraction zone 11 as lean solvent in the manner previously discussed. Make-up solvent as needed may be introduced into the system via line 13."

The above-described method utilizes a single distillation column, plus a separate rectifying zone, to recover the aromatic hydrocarbons and avoid solvent losses. However, because the bottoms fraction from the rectifying zone is returned to the lower portion of the stripper column, or alternately bypassed entirely, and then passed with bottoms from the stripper column to the top (raffinate end) of the extraction column, aromatic hydrocarbons present in the bottoms from the rectifying zone can be lost in the extractor raffinate, thereby reducing product recovery.

U.S. Pat. No. 3,702.295 discloses a method for aromatic hydrocarbon recovery that also utilizes the single column, vapor side-cut approach. However, this method differs from that disclosed in U.S. Pat. No. 3,590,092 in that the rectification zone is refluxed with the aqueous phase from the overhead condensate, instead of the hydrocarbon phase. Also, the bottoms fraction from the rectification zone is introduced to an intermediate section in the stripped column instead of the lower section. The side-cut aspect of this method is set forth at col. 6, lines 45 to 68 wherein it is stated that:

"The second vapor fraction comprising aromatic hydrocarbons, water and solvent which was withdrawn from an intermediate section of the stripping zone is then passed to a lower section of a rectification zone to separate therein the aromatic hydrocarbons from the sulfolane solvent. This separation is accomplished by maintaining the rectification zone under conditions including a temperature of about 100° F. to about 400° F. and a pressure of about 50 mm. Hg to about 25 psig, preferably 5 psig to about 20 psig, and withdrawing from an upper section of the rectification zone a vapor fraction relatively free of solvent comprising aromatic hydrocarbons and water (steam). This vapor fraction is condensed and the aromatics recovered are relatively free of non-aromatics and sulfolane solvent. At least a portion of the liquid water formed when the vapor fraction was condensed is passed to the upper section of the rectification zone to help effectively remove the sulfolane solvent from the aromatics. Withdrawn from a lower section of the rectification zone is a liquid stream comprising solvent and water. This stream is then passed, as reflux, to an intermediate section of the stripping zone to recover therein the sulfolane solvent for use in the extraction zone."

The above-described method utilizes a single distillation column, plus a rectification zone which can be incorporated into the single column, to recover the aromatic hydrocarbons and avoid solvent losses. However, because the bottoms fraction from the rectification zone is introduced to an intermediate section of the stripper column, no stripping benefit is obtained from it in the lower section of the stripping zone. Additional steam is supplied to the lower section of the stripper column for this purpose.

Processes other than the vapor side-cut type have also been proposed. For example, U.S. Pat. No. 3,714,003 discloses a process wherein the side-cut vapors are condensed and water-washed to remove solvent from the aromatic hydrocarbons. This process avoids the use of a rectification zone but requires the use of appropriate water-washing equipment such as extractors and mixer-settlers. This type of process can provide a particularly effective means of recovering aromatic hydrocarbons when certain aromatic-selective solvents, e.g., polyalkylene glycols, are used. The use of other solvents having a higher affinity for aromatic hydrocarbons, e.g., certain glycol ethers, may require further processing to avoid solvent losses.

U.S. Pat. No. 4,419,226 discloses a process that utilizes two distillation columns without a side-cut stream for the recovery of aromatic hydrocarbons and a non-aromatic raffinate stream from a hydrocarbon charge stock. The hydrocarbon charge stock is treated with an aromatics-selective solvent to provide an aromatics-rich solvent stream and a non-aromatic raffinate stream. The aromatics- rich solvent stream is treated in a stripper column at conditions to separate substantially all of the non-aromatic hydrocarbons therefrom. The rich solvent stream is subjected to steam stripping to provide a high purity aromatics stream and an aqueous stream comprising the steam condensate and solvent.

The above-described processes set forth various methods for recovering aromatic hydrocarbons from the extract phase from solvent extraction processes. The two distillation column approach offers sufficient design flexbility to accommodate most solvent-aromatic hydrocarbon combinations. Nonetheless, improved methods are sought for the recovery of extracted aromatic hydrocarbons that utilize a single column, side-cut approach and effectively avoid solvent losses.

SUMMARY OF THE INVENTION

The present invention provides methods for the recovery of extracted aromatic hydrocarbons while avoiding solvent losses.

One aspect of the invention provides a method which comprises introducing the extract phase containing aromatic hydrocarbons, contaminating non-aromatic hydrocarbons, and aromatic-selective solvent into an upper section of a stripping zone; introducing a stripping medium comprising rectification zone bottoms as hereinafter described into a lower section of the stripping zone; withdrawing from the upper section of the stripping zone a first vapor fraction comprising water and non-aromatic hydrocarbons; withdrawing from an intermediate section of the stripping zone a second vapor fraction comprising aromatic hydrocarbons, water and solvent; passing the second vapor fraction into a lower section of a rectification zone; withdrawing from an upper section of the rectification zone a third vapor fraction comprising aromatic hydrocarbons and water; condensing the third vapor fraction to provide a relatively non-aromatic and solvent free aromatic hydrocarbon stream and a liquid water stream; passing at least a portion of the liquid water stream into the upper section of the rectification zone; withdrawing from the lower section of the rectification zone a bottoms comprising solvent and water; passing at least a portion of said rectification zone bottoms to the lower section of the stripping zone as hereinbefore described; and withdrawing from the lower section of the stripping zone a lean solvent stream.

Another aspect of the invention provides a method which comprises introducing the extract phase containing aromatic hydrocarbons, contaminating non-aromatic hydrocarbons, and aromatic-selective solvent into an upper section of the stripping zone; introducing a stripping medium into the lower section of the stripping zone; withdrawing from the upper section of the stripping zone a first vapor fraction comprising water and non-aromatic hydrocarbons; withdrawing from an intermediate section of the stripping zone a second vapor fraction comprising aromatic hydrocarbons, water and solvent; passing the second vapor fraction into a lower section of a rectification zone; withdrawing from an upper section of the rectification zone a third vapor fraction comprising aromatic hydrocarbons and water; condensing the third vapor fraction to provide a relatively non-aromatic and solvent free aromatic hydrocarbon stream and a liquid water stream; passing at least a portion of the aromatic hydrocarbon stream into the upper section of the rectification zone; withdrawing from the lower section of the rectification zone a bottoms comprising solvent and aromatics; passing at least a portion of said rectification zone bottoms into an intermediate section of the stripping zone; and withdrawing from the lower section of the stripping zone a lean solvent stream.

DETAILED DESCRIPTION OF THE INVENTION

Figure 1:
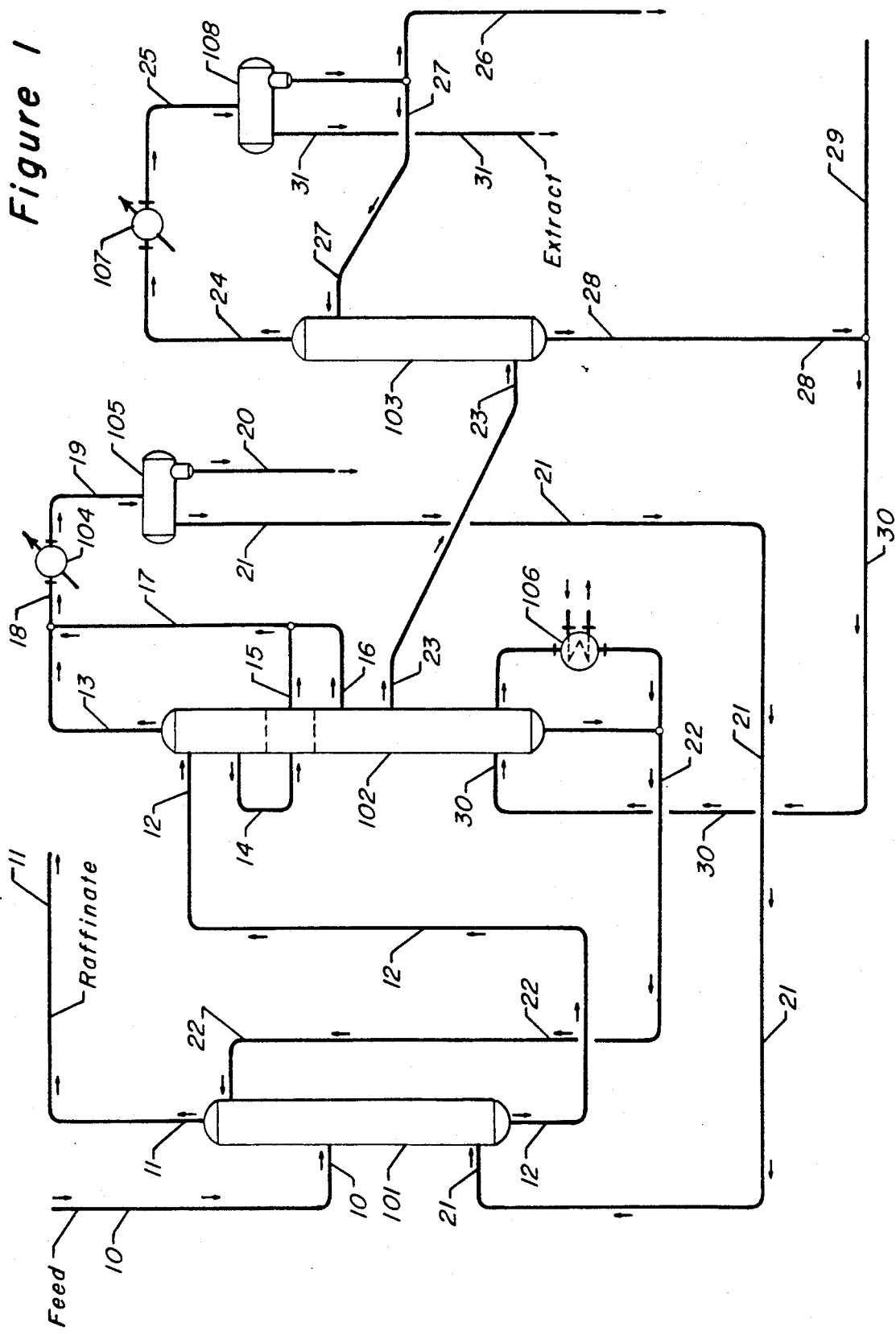
FIG. 1 is a schematic flow diagram of the method of the invention wherein the rectification zone is refluxed with the aqueous phase of the overhead condensate.

Hydrocarbon feedstocks suitable for utilization in the method of the present invention include many different aromatic-non-aromatic mixtures having a substantially high enough concentration of aromatic hydrocarbons to economically justify the recovery of the aromatic hydrocarbons as a separate product stream. The present invention is particularly applicable to hydrocarbon feed mixture containing at least 15% by weight aromatic hydrocarbons. Typical aromatic feedstock charged to an extraction step will contain from about 25% to about 75% by weight aromatic hydrocarbons with aromatic hydrocarbon concentrations as high as 95% being suitable in some instances. A suitable carbon range for the hydrocarbon feedstock is from about 5 carbon atoms per molecule to about 20 carbon atoms per molecule, and preferably from 5 to 10 carbon atoms per molecule.

One suitable source of hydrocarbon feedstock is a depentanized fraction from the effluent from a conventional catalytic reforming process unit for the reforming of a naphtha feedstock. Another suitable source of feedstock is the liquid by-product from a pyrolysis gasoline unit which has been hydrotreated to saturate olefins and diolefins, thereby producing an aromatic hydrocarbon concentrate suitable for the solvent extract technique described herein.

Still another suitable feed stream is a lube oil fraction such as a light distillates to heavy distillate, bright stock, etc., which have boiling points between about 400° F. and about 1200° F. The aromatic hydrocarbons present in heavy hydrocarbon feeds, e.g., lubricating oils, generally include: alkylbenzenes, indenes, tetralins, indenes, naphthalenes, fluorenes, acenaphthalenes, biphenyls, phenanltrenes, anthracenes, discenaphthalenes, pyrenes, chripenes, diaceanthracenes, benzyprenes and other various aromatic feed components.

A preferred feedstock for use in the present invention is one recovered from a catalytic reforming unit, comprises single ring aromatic hydrocarbons of the $C_6$-$C_9$ range which are also mixed with corresponding boiling range paraffins and naphthenes which are present in the product from a catalytic reforming unit.

Solvent compositions which may be utilized in the practice of the present invention are those selected from the classes which have high selectivity for aromatic hydrocarbons. These aromatic selective solvents generally contain one or more organic compounds containing in their molecule at least one polar group, such as a hydroxyl, amino, cyano, carboxyl or nitro radical. In order to be effective, the organic compounds of the solvent composition having the polar radical must have a boiling point substantially greater than the boiling point of water since water is preferably included in the solvent composition for enhancing its selectivity. In general, the solvent must also have a boiling point greater than the end boiling point of the aromatic component to be extracted from the hydrocarbon feed mixture.

Organic compounds suitable for use as part of the solvent composition are preferably selected from the group of those organic-containing compounds which include the aliphatic and cyclic alcohols, cyclic monomeric sulfones, the glycols and glycol ethers, as well as the glycol esters and glycol ether esters. The mono- and poly-alkylene glycols in which the alkylene group contains from 2 to 3 carbon atoms, such as ethylene glycol, diethylene glycol, triethylene glycol, and tetraethylene glycol, propylene glycol, dipropylene glycol, and triporpylene glycol, as well as the methyl, ethyl, propyl and butyl ethers of the glycol hydroxyl groups and the acetic acid esters thereof, constitute a satisfactory class of organic solvents useful in admixture with water as the solvent composition for use in the present invention.

Some of these solvents, when combined with other cosolvents, can provide mixed extraction solvents having desirable properties. When such mixed solvents are utilized, the preferred solvents are the low molecular weight polyalkylene glycols of the formula:

$$HO-[CHR_1-(CR_2R_3)_n-O]_m-H$$

wherein n is an integer from 1 to 5 and is preferably the integer of 1 or 2; m is an integer having a value of 1 or greater, preferably between about 2 to about 20 and most preferably between about 3 and about 8; and wherein $R_1$, $R_2$ and $R_3$ may be hydrogen, alkyl, aryl, araalkyl or alkylaryl and are preferably hydrogen and alkyl having between 1 and about 10 carbon atoms and most preferably are hydrogen. Examples of the polyalkylene glycol solvents employable herein are diethylene glycol, triethylene glycol, 1,3-butylene glycol, 1,2-butylene glycol, 1,5-pentaethylene glycol, and mixtures thereof and the like. Preferred solvents are diethylene glycol, triethylene glycol, tetraethylene glycol being most preferred. When a "cosolvent" component is employed herein such is preferably a glycol ether of the formula:

$$R_4O-[CH_5-(CHR_6-)-_xO]_y-R_7$$

wherein $R_4$, $R_5$, $R_6$ and $R_7$ may be hydrogen alkyl, aryl, aralkyl, alkylaryl and mixtures thereof with the provisio that $R_4$ or $R_7$ are not both hydrogen. The value of x is an integer from 1 to 5, preferably 1 or 2 and y may be an integer from 1 to 10 and is preferably from 2 to 7, and most preferably from 2 to 5. $R_4$, $R_5$, $R_6$ and $R_7$ are preferably selected from the group consisting of hydrogen and alkyl having 1 to about 10 carbons with the provisio that $R_4$ and $R_7$ may not both be hydrogen and most preferably $R_4$ is alkyl having from 1 to 5 carbons and $R_5$, $R_6$ and $R_7$ are hydrogen. The mixture(s) of solvent and cosolvent is selected such that at least one solvent and one cosolvent are provided to form the mixed extraction solvent. The cosolvent generally comprises between about 0.1 and about 99 percent of the mixed extraction solvent, preferably between about 0.5 and about 80 percent and more preferably between about 5 and about 60 percent by weight based on the total weight of the mixed extraction solvent. The above-described mixed extraction solvents are fully disclosed in U.S. Pat. No. 4,498,980, hereby incorporated by reference.

Another typical aromatics-selective solvent utilized in commercial aromatic extraction processes which can be recovered in accordance with the practice of this invention, is commonly referred to as sulfolane (tetrahydrothiphene, 1-1 dioxide). Also employed are those sulfolane derivatives corresponding to the structural formula:

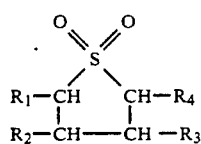

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms. Other solvents which may be included within this process are the sulfolenes, such as 2-sulfolene or 3-sulfolene which have the following structures:

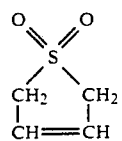

Other typical solvents which have a high selectivity for separating aromatics from non-aromatic hydrocarbons and which may be processed within the scope of the present invention are 2-methylsulfolane, 2,4-dimethylsulfolane, methyl-2- sulfonyl ether, N-aryl-3-sulfonylamine, 2-sulfonyl acetate, dimethylsulfoxide, N-methyl pyrrolidone, etc.

A particularly preferred solvent of the above-described sulfolane type has the following structural formula:

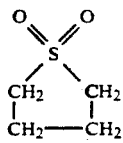

The aromatic selectivity of the solvent can usually be enhanced by the addition of water to the solvent. Preferably, the solvents utilized in the practice of this invention contain small quantities of water in order to increase the selectivity of the overall solvent phase for aromatic hydrocarbons without reducing substantially the solubility of the solvent phase for aromatic hydrocarbons. Accordingly, the solvent composition of the present invention preferably contains from about 0.1% to about 20% by weight water and, preferably, about 0.5 to about 10% by weight depending upon the particular solvent utilized and the process conditions at which the extraction zone and the extractor-stripper are operated.

Aromatic hydrocarbons contained in the foregoing feedstocks are recovered by introducing the hydrocarbon feedstock into a solvent extraction zone maintained under solvent extraction conditions including the presence of an aromatic selective solvent of the type discussed. Solvent extraction conditions and techniques are generally well known to those trained in the art and vary, depending on the particular aromatic selective solvent utilized.

The solvent extraction zone provides an extract phase comprising solvent having aromatic hydrocarbons and a minor amount of non-aromatic hydrocarbons dissolved therein and a raffinate phase comprising non-aromatic hydrocarbons. Typically, the raffinate is water washed to remove any solvent which may be in solution and entrained therein. In the present invention, this water is preferably provided by the aqueous overhead condensate from the rectification zone as hereinafter described. Preferably, the extraction conditions utilized are correlated to maintain the solvent and hydrocarbons passed to the extraction zone in the liquid phase so as to embody a liquid phase solvent extraction. The conditions, apparatus, and mode of operation associated with the solvent extraction zone are well known to those trained in the art. For example, see U.S. Pat. Nos. 3,714,003, 4,419,226, and 4,781,820, hereby incorporated by reference.

Also embodied within the solvent extraction zone is the concept of displacing heavier non-aromatic hydrocarbons from the extract phase at the lower end of the solvent extraction zone by utilizing the known technique of a recycling from the overhead of the stripping column hydrocarbon containing reflux at that point. By displacing the heavy non-aromatics with light non-aromatics, the resulting non-aromatics are more readily separable from the aromatics in the subsequent stripping zone to be discussed later. It is preferred that this reflux stream comprise relatively light non-aromatic hydrocarbons but significant quantities of aromatic hydrocarbons, i.e., 30% to 60% by weight, may be present in the reflux stream. The exact amount of reflux introduced into the lower section of the solvent extraction zone varies depending on the degree of non-aromatic hydrocarbon rejection desired in the extraction zone. Preferably, the reflux is at least 10% by volume of the extract phase so as to insure effective displacement of the heavy non-aromatic hydrocarbons from the extract phase into the raffinate. According to the process of the present invention at least a portion, if not all, of the light non-aromatic reflux required is provided by a non-aromatic fraction removed as overhead from an upper section of a hereinafter described stripping zone. This fraction is withdrawn as a vapor and contains water (steam) which is preferably condensed and removed before the non-aromatics are passed as reflux to the solvent extraction zone.

The solvent extraction zone is operated under conventional conditions including elevated temperature and a sufficiently elevated pressure to maintain the solvent reflux and hydrocarbon charge stream in the liquid phase. When utilizing a solvent such as sulfolane, suitable temperatures are about 80° F. to about 400° F., preferably about 175° F. to about 300° F., and suitable pressures are about atmospheric to about 400 psig, preferably about 50 to 150 psig. Solvent quantities should be sufficient to dissolve substantially all of the aromatic hydrocarbons present in the hydrocarbon feed to the extraction zone. Preferred are solvent to feed ratios, by volume, of about 2:1 to about 10:1 when utilizing a $C_6$-$C_9$ range naptha cut as feed.

The extract phase from the solvent extraction zone comprising solvent, aromatic hydrocarbons and contaminating non-aromatic hydrocarbons is introduced into an upper section of a stripping zone to remove therein, the non-aromatic hydrocarbons. This separation is accomplished by introducing a stripping medium, e.g., steam., into a lower section of the stripping zone in amounts necessary to remove essentially all of the contaminating amounts of non-aromatic hydrocarbons from the extract phase as a first vapor fraction which is withdrawn from the upper section of the stripping zone. This vapor fraction comprises water (steam), non-aromatic hydrocarbons, and an amount of aromatic hydrocarbons. This vapor fraction is preferably cooled and condensed to form an aqueous phase and a hydrocarbon phase. This hydrocarbon phase is then recovered and passed to the lower section of the solvent extraction zone to serve as the described light non-aromatic reflux and to recover the aromatic hydrocarbons contained in the original vapor fraction withdrawn from the upper portion of the stripping column. The aromatic hydrocarbons are then recovered by withdrawing from an intermediate section of the stripping zone a second vapor fraction comprising aromatic hydrocarbons and solvent.

The exact conditions to be utilized in a stripping zone of the type described are broadly within a temperature range of about 200° F. to about 500° F. and a pressure range of about 50 mm. Hg absolute to about 25 psig and more preferably from about 1 psig to about 20 psig. As is well known to those trained in the art, more exact processing conditions are a function of a myriad of variables, particularly feed compositions, aromatic purity desired and aromatic recovery sought. However, based on the teaching herein, it is within the scope of one trained in the art to readily develop specific processing conditions for a given feedstock.

The second vapor fraction comprising aromatic hydrocarbons, water and solvent which was withdrawn from an intermediate section of the stripping zone is then passed to a lower section of a rectification zone to separate therein the aromatic hydrocarbons from the solvent. This separation is accomplished by maintaining the rectification zone under conditions including a temperature of about 100° F. to about 400° F. and a pressure of about 50 mm. Hg to about 25 psig, preferably 1 psig to about 15 psig, and withdrawing from an upper section of the rectification zone a vapor fraction relatively free of solvent comprising aromatic hydrocarbons and water (steam). This vapor fraction is condensed and the aromatics recovered are relatively free of non-aromatics and solvent.

In one aspect of the present invention, the extract is removed as product and at least a portion of the aqueous phase of the condensate is returned to an upper section of the rectification zone as reflux. Any remaining portions of the aqueous phase are preferably used to wash the raffinate from the extractor. At least a portion, and preferably all, of the bottoms from the rectification zone are then passed to a lower section of the stripping zone to provide stripping medium in the stripping zone. It is to be noted that the rectifier bottoms can be heat-exchanged with other streams, e.g., the bottoms from the stripping zone, to vaporize the stripping medium prior introducing it into the stripping zone. An important feature of this aspect of the present invention is that the introduction of the rectification zone bottoms into the lower section of the stripping zone instead of an intermediate section, provides stripping benefit in the lower section of stripping zone as well as the intermediate section. Moreover, as a result the flowrate of stripping medium throughout the stripping zone can be reduced and accordingly energy savings can be realized. The rectification zone bottoms is preferably combined with spent raffinate wash water prior to introducing it into the stripping zone in order to provide additional stripping medium.

In another aspect of the present invention, the aqueous phase of the overhead condensate is not used to reflux the rectification zone. Instead, at least a portion of the extract phase is returned to an upper portion of the rectification zone as reflux. Any remaining portions are preferably removed as product. The aqueous phase is, preferably, used to wash the raffinate. At least a portion, and preferably all, of the bottoms product of the rectification zone is returned to an intermediate section of the stripper column, preferably at about the same location, e.g., one tray below the location from which the second vapor fraction, i.e., side-cut, is withdrawn. An important feature of this aspect of the present invention is that the introduction of the rectification zone bottoms into an intermediate section of the stripper column avoids the potential loss of aromatic product through the stripper bottoms into the raffinate from the extractor as hereinbefore described.

DESCRIPTION OF THE DRAWINGS

Figure 2:
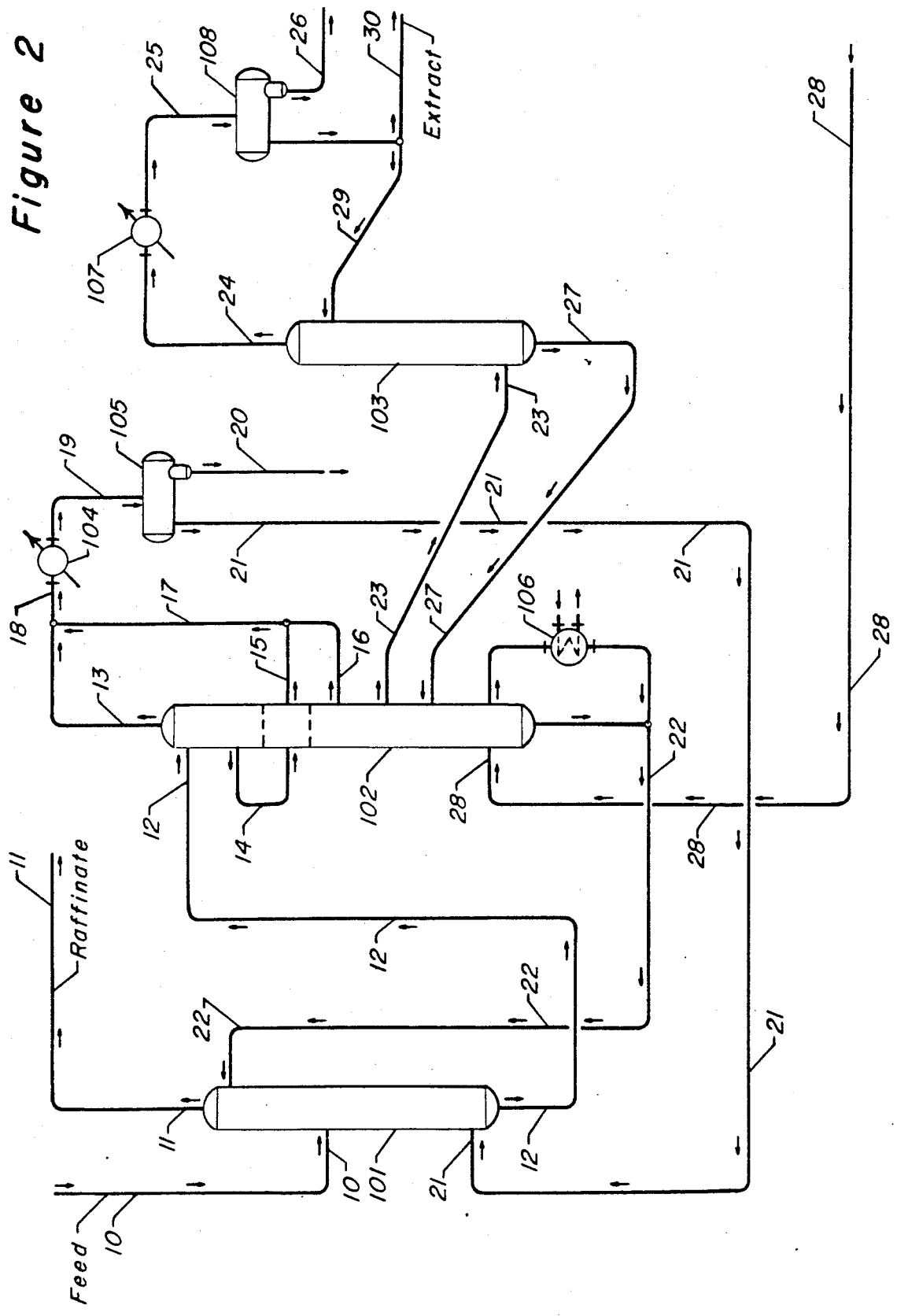
FIG. 2 is a schematic flow diagram of the method of the invention wherein the rectification zone is refluxed with the hydrocarbon phase of the overhead condensate.

The further description of the method of this invention is presented with reference to the attached schematics, FIG. 1 and FIG. 2. The figures represent preferred aspects of the invention and are not intended to be a limitation on the generally broad scope of the invention as set forth in the claims. Of necessity, some miscellaneous appurtenances including valves, pumps, separators, heat exchangers, reboilers, etc., have been eliminated. Only those vessels and lines necessary for a complete and clear understanding of the process of the present invention are illustrated, with any obvious modifications made by those possessing expertise in the art of aromatic solvent extraction.

Referring to FIG. 1.

A $C_6$ to $C_9$ cut of depentanized reformate containing aromatic hydrocarbons and non-aromatic hydrocarbons is passed via line 10 to extractor 101 maintained at extraction conditions, along with lean solvent via line 22 and reflux via line 21, the sources of which are hereinafter described. A raffinate stream containing non-aromatic hydrocarbons and solvent is removed from extractor 101 via line 11, cooled to separate a portion of the dissolved solvent out of solution (not shown), said recovered solvent can be recycled to extractor 101 and introduced (not shown) at or near the feed point of line 10. Alternately, this stream can be added to the lean solvent stream, line 22. The hydrocarbon raffinate phase can then be washed with water from the overhead aqueous phase condensate of rectification zone 103, i.e., line 26, which is substantially free of solvent. An extract stream containing aromatic hydrocarbons, non-aromatic hydrocarbons, solvent and water is removed from extractor 101 via line 12 and passed to an upper section of stripper column 102, which is essentially a distillation zone containing at least one vaporizing section which functions to flash off and vaporize a portion of the non-aromatic hydrocarbon contaminants contained in the extract phase in line 12. A preferred form of the stripping column comprises a vertical column containing three distinct sections; that is, an uppermost primary flashing section; a lower or intermediate flashing or vaporizing section, and a lowermost stripping section vapor sealed from the upper sections of the column and wherein true stripping of the rich solvent is obtained.

The operating conditions in stripping column 102 may be varied widely, but generally the conditions are one of essentially at or above atmospheric pressure; although, in some cases, the upper portion may be maintained under vacuum conditions. Therefore, in a broad sense, stripper column 102 operates under a pressure from 50 mm. Hg to absolute to 25 psig and a temperature from 200° F. to 500° F.

Returning now to the operation of stripper column 102, the rich solvent phase, as previously mentioned, is introduced into the upper section at superatmospheric pressure, e.g., 25 psig and a temperature of about 200° F. to about 250° F. Under these conditions, a portion of the non-aromatic hydrocarbons is flashed off and removed via line 13. The remainder of the extract phase is now passed via connecting line 14 into another vaporizing section wherein another portion of the non-aromatic hydrocarbons is vaporized and removed from the column as a vapor stream via line 15. Finally, the residue of the extract stream now comprising solvent having the desired aromatic hydrocarbons dissolved therein, but still containing non-aromatic hydrocarbons is passed into the lower stripping section wherein a true stripping operation takes place.

The lowermost section of stripper column 102 is typically maintained at a pressure of from 1 to 10 psig, typically about 3 psig. and a temperature of from 180° F. to 300° F., typically, about 220° F. at the drawoff point for the remainder of the non-aromatic hydrocarbons via line 16, and typically a pressure of from about 10 psig to 15 psig and a temperature of 280° F. to 320° F. at the bottom of stripper column 102. Stripping medium, e.g., steam comprising spent raffinate wash water, aqueous overhead condensate from stripper column 102 and rectification zone bottoms, line 28, is introduced to the lower section of stripper 102 via line 30. The remainder of the non-aromatic hydrocarbons is removed via line 16 and combined with the non-aromatic hydrocarbons removed via line 15 and combined via line 17 with line 13, thereafter passed via line 18 to condensor 104 and then to tank 105 via line 19. Non-aromatic hydrocarbon condensate from tank 105 is then passed as reflux to extractor 101 via line 21. The aqueous phase condensate from tank 105, i.e., line 20, which contains water and solvent, is combined with spent raffinate wash water (not shown) and passed to stripper 102 as stripping medium via line 29.

A side-cut vapor fraction is removed from an intermediate section of stripper column 102 via line 23 and passed to rectification zone 103 which is maintained under rectifying conditions. Typically, the conditions maintained in rectification zone 103 include a temperature of from about 200° F. to 250° F. and a pressure of from about 1 to 10 psig. An overhead stream comprising the desired aromatic hydrocarbons, i.e., benzene, toulene, zylene, (BTX), is withdrawn via line 24, passed through condensor 107, then passed to tank 108 via line 25. The aromatics extract phase is removed as product via line 31. A portion of the overhead aqueous condensate is returned to rectification zone 103 via line 27 as reflux. The remainder, line 26, is preferably used as raffinate wash water (not shown) and the spent raffinate wash water is preferably used as stripping medium in stripper column 102, i.e., passed via line 29. The bottoms from rectification zone 103 which contains solvent and water is passed via line 28 to stripper column 102 via line 30 as hereinbefore described.

The following table sets forth a typical material balance and temperatures and pressures around the rectification zone of FIG. 1 for BTX with a mixed tetraethylene glycol/methoxytriglycol solvent commercially known as CAROM solvent, which is obtainable from UOP, Des Plaines, Ill.

| Line No. | 23 | 24 | 31 | 26 | 27 | 28 |
|---|---|---|---|---|---|---|
| Total Flow (lb/hr) | 36504 | 35820 | 28753 | 3534 | 3533 | 4217 |
| BTX Flow (lb/hr) | 28714 | 28714 | 28704 | 5 | 5 | 5 |
| Water Flow (lb/hr) | 6902 | 7106 | 49 | 3529 | 3528 | 3324 |
| CAROM Flow (lb/hr) | 888 | — | — | — | — | 888 |
| CAROM Conc. | 2.4 wt % | 1 ppm | 1 ppm | 1 ppm | 1 ppm | 21.1 wt % |
| Temperature, °F. | 237 | 200 | 130 | 130 | 130 | 203 |
| Pressure, psig | 7.6 | 6.6 | 6.6 | 6.6 | 6.6 | 7.6 |

Referring to FIG. 2.

The description hereinbefore presented with reference to FIG. 1 is applicable here unless otherwise set forth below.

The overhead aqueous condensate phase from tank 108, line 26, is not used to reflux rectification zone 103. Instead, a portion of the extract phase is returned to rectification zone 103 via line 29 as reflux. The remainder of the aromatics extract phase is removed as product via line 30. The bottoms from the rectification zone 103, which contains aromatics and solvent, is passed via line 27 to an intermediate section of stripper column 102, i.e., just below the point of side-cut removal, line 23. Spent raffinate wash water is passed to stripper column 102 via line 28.

The following table sets forth a typical material balance and temperatures and pressures around the rectification zone of FIG. 2 for BTX with the CAROM solvent described above.

| Line No. | 23 | 24 | 30 | 26 | 29 | 27 |
|---|---|---|---|---|---|---|
| Total Flow (lb/hr) | 38780 | 40018 | 28812 | 6901 | 4305 | 3067 |
| BTX Flow (lb/hr) | 30948 | 33070 | 28763 | 9 | 4298 | 2176 |
| Water Flow (lb/hr) | 6944 | 6948 | 49 | 6892 | 7 | 3 |
| CAROM Flow (lb/hr) | 888 | — | — | — | — | 888 |
| CAROM Conc. | 2.3 wt % | 1 ppm | 1 ppm | 1 ppm | 1 ppm | 29 wt % |
| Temperature, °F. | 236 | 202 | 130 | 130 | 130 | 210 |
| Pressure, psig | 7.6 | 6.6 | 6.6 | 6.6 | 6.6 | 7.6 |

In addition to the aspects of the invention disclosed above, those skilled in the art will readily appreciate other variations within the scope of the claims set forth below. For example, the rectification zone can be incorporated into the stripping zone as a single column and provide appropriate internal and external piping to accommodate the flows. Also, it might be desirable in some instances to utilize a reboiler on the rectification zone in order to prevent aromatics condensation. Furthermore, the method can incorporate other miscellaneous steps such as washing, mixing, setting, decanting, as well as various purge and make-up streams and heat exchange schemes.

I claim as my invention:

1. In a method for recovering aromatic hydrocarbons from an extract phase from an aromatic-selective, solvent extraction zone which comprises the steps of:

(a) introducing the extract phase containing aromatic hydrocarbons, non-aromatic hydrocarbons and aromatic-selective solvent into an upper section of a stripping zone;

(b) introducing a stripping medium into a lower section of the stripping zone;

(c) withdrawing from the upper section of the stripping zone a first vapor fraction comprising water and non-aromatic hydrocarbons;

(d) withdrawing from a point at an intermediate section of the stripping zone a second vapor fraction comprising aromatic hydrocarbons, water and solvent;

(e) passing the second vapor fraction to a rectification zone;

(f) withdrawing from an upper section of the rectification zone a third vapor fraction comprising aromatic hydrocarbons and water;

(g) condensing the third vapor fraction to provide an aromatic hydrocarbon stream and a liquid water stream;

(h) passing at least a portion of the aromatic hydrocarbon stream into the upper section of the rectification zone;

(i) withdrawing from the lower section of the rectification zone a rectification zone bottoms comprising solvent and aromatic hydrocarbons;

(j) passing at least a portion of said rectification zone bottoms to the stripping zone; and (k) withdrawing from the lower section of the stripping zone a stripper bottoms stream comprising aromatic selective solvent; the improvement which comprises introducing substantially the entire rectification zone bottoms at or near the point in the intermediate section of the stripping zone where the second vapor fraction is withdrawn.

2. The method of claim 1 wherein said aromatic selective solvent comprises a polyalkene glycol.

3. The method of claim 2 wherein said aromatic selective solvent comprises tetraethylene glycol.

4. The method of claim 1 wherein said aromatic selective solvent comprises a polyalkylene glycol of the formula:

$$HO-[CHR_1-(CH_2R_3)_n-O-]_mH$$

wherein n is an integer from 1 to 5 m is an integer having a value of 1 or greater and $R_1$, $R_2$ and $R_3$ may each be hydrogen, alkyl, aryl, araalkyl, alkylaryl and mixtures thereof and a glycol ether of the formula:

$$R_4O-[CHR_5-(CHR_6)_xO]_y-R_7$$

wherein $R_4$, $R_5$, $R_6$ and $R_7$ may each be hydrogen, alkyl, aryl, araalkyl, alkylaryl and mixtures thereof with the proviso that $R_4$ and $R_7$ are not both hydrogen; x is an integer from 1 to 5; and y may be an integer from 2 to 10;

5. The method of claim 4 wherein said aromatic selective solvent consists essentially of a polyalkylene glycol selected from the class consisting of diethylene glycol, triethylene glycol, tetraethylene glycol and mixtures thereof and a glycol ether selected from the class consisting of methoxytriglycol, ethoxytriglycol, butoxytriglycol, methoxytetraglycol and ethoxytetraglycol and mixtures thereof wherein the glycol either comprises between about 0.1 and 99 percentage by weight of the mixed extraction solvent.

6. The process of claim 5 wherein the polyalkylene glycol is tetraethylene glycol and the glycol ether is methoxytriglycol.

7. The method of claim 1 wherein said aromatic selective solvent comprises a compound having the following formula:

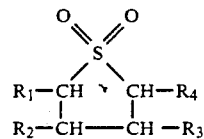

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms.

* * * * *